United States Patent
Yago (10) Patent No.: US 10,121,242 B2
(45) Date of Patent: Nov. 6, 2018

(54) IMAGE INSPECTION APPARATUS AND IMAGE FORMING SYSTEM

(71) Applicant: KONICA MINOLTA, INC., Chiyoda-ku, Tokyo (JP)

(72) Inventor: Hiroaki Yago, Hino (JP)

(73) Assignee: Konica Minolta, Inc., Chiyoda-ku, Tokyo (JP)

( * ) Notice: Subject to any disclaimer, the term of this patent is extended or adjusted under 35 U.S.C. 154(b) by 0 days.

(21) Appl. No.: 15/783,084

(22) Filed: Oct. 13, 2017

(65) Prior Publication Data

US 2018/0130192 A1 May 10, 2018

(30) Foreign Application Priority Data

Nov. 7, 2016 (JP) .................................. 2016-217236

(51) Int. Cl.
*G06T 7/00* (2017.01)
*G01N 21/89* (2006.01)
*G03G 15/00* (2006.01)
*H04N 1/00* (2006.01)

(52) U.S. Cl.
CPC ............. *G06T 7/001* (2013.01); *G01N 21/89* (2013.01); *G03G 15/5062* (2013.01); *H04N 1/00326* (2013.01); *G06T 2207/30144* (2013.01)

(58) Field of Classification Search
CPC combination set(s) only.
See application file for complete search history.

(56) References Cited

U.S. PATENT DOCUMENTS

| | | | |
|---|---|---|---|
| 9,986,105 B2* | 5/2018 | Shojaku | H04N 1/00039 |
| 2006/0062441 A1* | 3/2006 | Nishida | H04N 1/6033 382/128 |
| 2013/0250319 A1* | 9/2013 | Kaneko | G06K 9/03 358/1.9 |
| 2013/0301070 A1* | 11/2013 | Saisho | G06T 7/001 358/1.13 |
| 2014/0270397 A1* | 9/2014 | Sochi | G06T 7/001 382/112 |
| 2014/0341437 A1* | 11/2014 | Araki | G06T 7/001 382/112 |

FOREIGN PATENT DOCUMENTS

JP 2006-182461 A 7/2006

* cited by examiner

*Primary Examiner* — Tsung-Yin Tsai
(74) *Attorney, Agent, or Firm* — Buchanan Ingersoll & Rooney PC (57) ABSTRACT

An image inspection apparatus includes: a storage that stores output image data used in forming an image on a paper sheet; a conveyor that conveys the paper sheet; a reader that reads the image during conveyance, and generates read image data; a determiner that compares pixels in the read image data with corresponding pixels in the output image data, and determines whether the read image data matches the output image data; a circulator that circulates the paper sheet, and returns the paper sheet to the reader; and a controller that controls the circulator to circulate the paper sheet and return the paper sheet to the reader when a mismatch is detected by the determiner, wherein the reader generates circulated read image data when the paper sheet is circulated and conveyed, and the determiner determines whether the image is normal or abnormal depending on the result of comparison.

12 Claims, 10 Drawing Sheets

IMAGE INSPECTION APPARATUS AND IMAGE FORMING SYSTEM

Japanese Patent Application No. 2016-217236 filed on Nov. 7, 2016, including description, claims, drawings, and abstract the entire disclosure is incorporated herein by reference in its entirety.

BACKGROUND

Technological Field

The present invention relates to a technology for accurately determining whether an image formed on a paper sheet output from an image forming apparatus is normal.

Description of the Related Art

There is an image forming system that includes a reading device (a printout reading device) connected to the latter stage of an image forming apparatus that forms an image on a paper sheet. The image forming system reads the image formed on the paper sheet with the reading device. There also is an image forming apparatus that includes a reader (a scanner that is a printout reader) on the downstream side of an image forming unit that forms an image on a paper sheet. The image forming apparatus reads the image formed on the paper sheet with the reader.

Stability is required in printed materials these days, and there is a demand for a mechanism for promptly and accurately spotting defects in printed materials so that defective printed materials will not leak to the market. To satisfy such a demand, there is a technology for optimizing an output image by conducting printed data inspection on read image data generated by reading the output image. In this technology, the read image data of the output image needs to be optimized by image processing, and inspection with a higher degree of accuracy needs to be conducted.

For example, in a case where a defect is detected as a result of inspection, it is extremely difficult to correctly determine whether the defect is of the printed material, whether the defect is due to electrical abnormality caused by disturbance noise, and whether the defect is sensed from a smudged portion of the reader. It is also extremely difficult to distinguish these causes of defects from one another.

In this case, to avoid outputting a defective printed material as a normal printed material, it is necessary to issue a notification about a printed material that is assumed to be defective as a result of inspection, and a user then determines whether the printed material mentioned in the notification is defective.

JP 2006-182461 A suggests various techniques related to this kind of technology.

According to JP 2006-182461 A, an image reading unit includes a read glass plate, an image sensor unit that reads a document being conveyed on the read glass plate, and a movement mechanism that changes the relative positions of the read glass plate and the image sensor unit. A background color switching unit includes a plate-like background member formed with a write-color member and a black-color member that are arranged to face the image reading unit. The background color switching unit switches the background color in the image reading optical path of the image reading unit between black and white. In accordance with the data of each pixel in the white-color member read by the image sensor unit, dust on the read glass plate is detected, and the image sensor unit is moved to a position where no dust is to be detected.

That is, the background color is switched to black or white by the reading unit, and dust is detected. When the dust is detected, the image sensor unit is moved so as to avoid the dust. In this case, the reading unit needs to be equipped with a background color switching mechanism. As a result, it becomes difficult to use a general-purpose sensor in the reading unit. There also are problems that cannot be solved at all when there is electrical noise.

SUMMARY

An object of the present invention is to provide an image inspection apparatus and an image forming system that are capable of accurately determining whether an image formed on a paper sheet output from an image forming apparatus is normal, and conducting accurate inspection so that each normal paper sheet is output while any abnormal paper sheet is not output.

To achieve the abovementioned object, according to an aspect of the present invention, an image inspection apparatus reflecting one aspect of the present invention comprises: a storage that stores output image data used in forming an image on a paper sheet; a conveyor that conveys the paper sheet on which the image is formed; a reader that reads the image formed on the paper sheet during conveyance being performed by the conveyor, and generates read image data; a determiner that compares pixels in the read image data with corresponding pixels in the output image data, and determines whether the read image data matches the output image data; a circulator that circulates the paper sheet from which the image has been read by the reader, and returns the paper sheet to the reader; and a controller that controls the circulator to circulate the paper sheet and return the paper sheet to the reader when a mismatch is detected by the determiner, wherein the reader generates circulated read image data when the paper sheet is circulated and conveyed to the reader, when a match is detected as a result of comparison between the read image data and the output image data, the determiner determines that the image formed on the paper sheet is normal, when a match is detected as a result of comparison between the circulated read image data and the output image data, the determiner determines that the image formed on the paper sheet is normal, and when a mismatch is detected as a result of comparison between the circulated read image data and the output image data, the determiner determines that the image formed on the paper sheet is abnormal.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, an image inspection apparatus and an image forming system according to one or more embodiments of the present invention will be described in detail with reference to the drawings. However, the scope of the invention is not limited to the disclosed embodiments.

[Configuration (1)]

Figure 1:
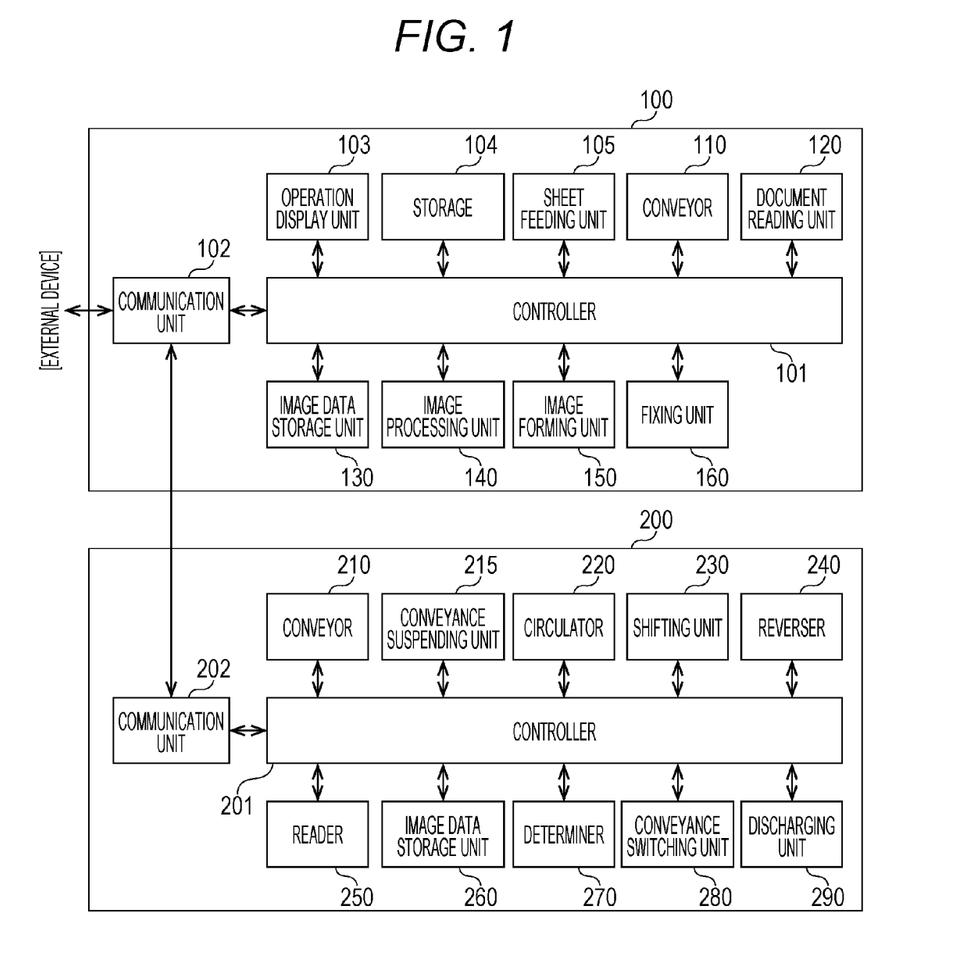
FIG. 1 is a diagram showing a configuration according to an embodiment of the present invention.
Figure 2:
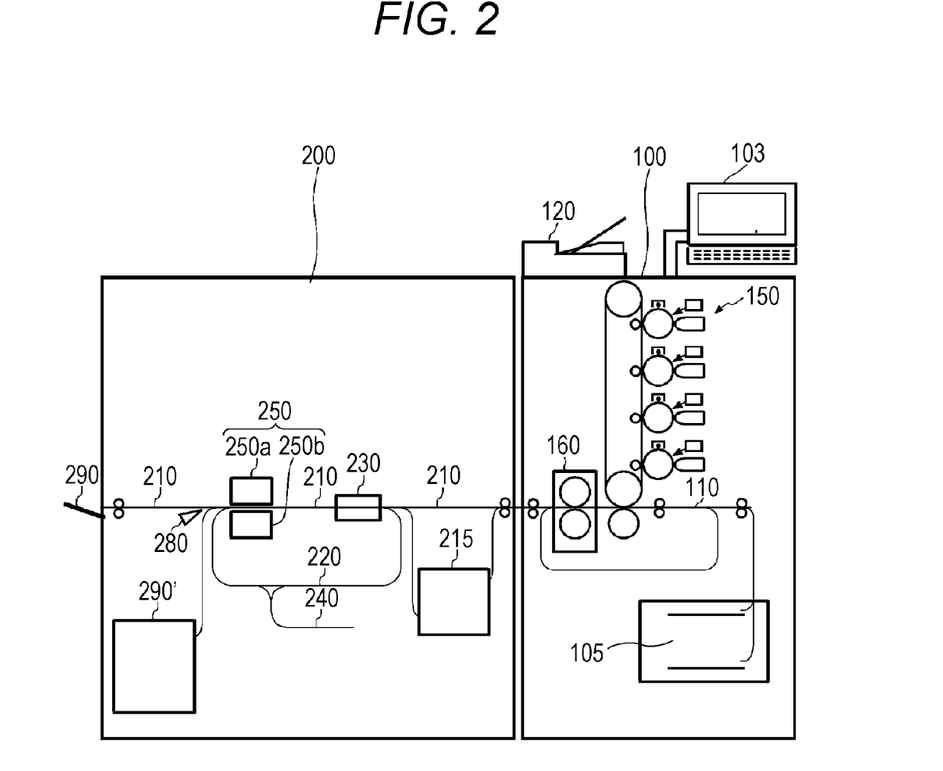
FIG. 2 is a diagram showing the configuration according to the embodiment of the present invention.

Referring now to FIGS. 1 and 2, a first example configuration of an image inspection apparatus and an image forming system is described in detail. In this example, an image forming apparatus 100 and an image inspection apparatus 200 are connected in the direction of sheet conveyance, to form an image forming system.

The image forming apparatus 100 includes: a controller 101 that controls the respective components in the image forming apparatus 100; a communication unit 102 for communicating with another device connected to the apparatus; an operation display unit 103 that accepts an operation input from a user and displays a state of the image forming apparatus 100; a storage 104 that stores various kinds of settings; a sheet feeding unit 105 that can feed paper sheets stored in a sheet feed tray into the apparatus; a conveyor 110 that conveys paper sheets inside the apparatus; a document reading unit 120 that reads an image of a document with an imaging element; an image data storage unit 130 that stores image data and various kinds of data at a time of image formation; an image processing unit 140 that performs various kinds of image processing necessary for image formation; an image forming unit 150 that forms an image on a paper sheet in accordance with an image formation instruction and image data; and a fixing unit 160 that fixes a toner-formed image onto a paper sheet with heat and pressure.

As shown in FIG. 2, for example, the image forming unit 150 includes: an image carrier on which a toner image is formed; a charging unit that electrically charges the image carrier at a predetermined potential; an exposing unit that forms an electrostatic latent image by exposing the electrically charged image carrier in accordance with image data; a developing unit that develops and turns the electrostatic latent image into a toner image; an intermediate transfer member on which toner images on image carriers of respective colors are combined; and a transfer unit that transfers the toner image on the intermediate transfer member onto a paper sheet. Here, the image forming unit 150 forms images in various colors, but may be formed with a single-color image forming unit.

The image inspection apparatus 200 is located on the downstream side in the sheet conveying direction of the image forming apparatus 100. The image inspection apparatus 200 includes: a controller 201; a communication unit 202; a conveyor 210 that conveys a paper sheet to be read; a conveyance suspending unit 215 that suspends the conveyance by temporarily stopping the conveyance of yet-to-be-read a paper sheet; a circulator 220 that circulates a read paper sheet and causes the read paper sheet to be re-read; a shifting unit 230 that moves a paper sheet in a direction that is in the plane of the paper sheet and is perpendicular to the sheet conveyance by the conveyor 210; a reverser 240 that reverses a paper sheet at the time of the conveyance by the conveyor 210 or the circulation by the circulator 220; a reader 250 that generates read image data by reading an image formed on a paper sheet; an image data storage unit 260 that stores the output image data used by the image forming unit 150 in forming an image on a paper sheet; a determiner 270 that compares the pixels in read image data with the corresponding pixels in output image data, and determines whether the pixels match the corresponding pixels; a conveyance switching unit 280 that switches sheet conveyance paths in accordance with the result of the determination made by the determiner 270; and an ejecting unit 290 that outputs normal images but does not output abnormal images.

Here, an image that is formed on a paper sheet and is output by the image forming apparatus 100 is read during conveyance in the image inspection apparatus 200.

Here, the reader 250 is designed to read both sides of a paper sheet with a first-side reader 250a that reads a first side of a paper sheet (the front side of the paper sheet, for example), and a second-side reader 250b that reads a second side of the paper sheet (the back side of the paper sheet, for example).

In the above described configuration, in a case where a match is detected as a result of comparison between read image data and output image data, the determiner 270 determines that the image formed on the paper sheet is normal. In a case where a match is detected as a result of comparison between circulated read image data and output image data, the determiner 270 determines that the image formed on the paper sheet is normal. In a case where a mismatch is detected as a result of comparison between circulated read image data and output image data, the determiner 270 determines that the image formed on the paper sheet is abnormal.

The determiner 270 also senses abnormality of read image data from a synchronization signal or a valid region signal included in the read image data generated by the reader 250. In a case where abnormality is detected by the determiner 270, the controller 201 controls the circulator 220 to return the paper sheet to the reader 250 through circulation performed by the circulator 220. Further, in a case where a mismatch is detected as a result of comparison between read image data and output image data, and a mismatch is detected as a result of comparison between circulated read image data and output image data, if these mismatches have occurred at different pixels, the determiner 270 determines that the image formed on the paper sheet is normal.

Further, in a case where a mismatch is detected as a result of comparison between read image data and circulated read image data, or where a mismatch is detected as a result of comparison between sets of circulated read image data obtained through circulating processes, the determiner 270 eliminates the pixel from which the mismatch is detected from the comparison objects, and then compares read image data with output image data or compares circulated read image data with output image data.

Meanwhile, the shifting unit 230 moves the same paper sheet by different amounts during the conveyance operations performed on the paper sheet by the conveyor 210 before and after circulation performed by the circulator 220. Further, in a case where a mismatch is detected as a result of comparison between read image data and output image data, and a mismatch is detected as a result of comparison between circulated read image data and output image data, if these mismatches have occurred at the pixels located in the positions equivalent to the shifting performed by the shifting unit 230 on the paper sheet, the determiner 270 determines that the abnormality is of the reader 250, and the image formed on the paper sheet is normal.

Also, in a case where mismatches have occurred at the same pixel, the determiner 270 determines that the image formed on the paper sheet is abnormal.

Further, during conveyance by the conveyor 210 or circulation by the circulator 220, the paper sheet is reversed by the reverser 240. During conveyance by the conveyor 210 and during circulation by the circulator 220, the reader 250 reads the image formed on the paper sheet with the first-side reader 250a and the second-side reader 250b, which are different reading means.

Also, in a case where mismatches are detected as a result of comparison prior to circulation and comparison after the circulation involving a reversal, and the mismatches have occurred at different pixels, the image formed on the paper sheet is determined to be normal. If these mismatches have occurred at the same pixel, the image formed on the paper sheet is determined to be abnormal.

When a paper sheet is circulated by the circulator 220 and is conveyed, the conveyor 210 also switches the conveyance speed to a lower speed. When a paper sheet is circulated and conveyed, the reader 250 generates circulated read image data with a higher resolution than that of read image data. After determining the reader 250 to be abnormal, the determiner 270 also eliminates the pixel from which a mismatch is detected due to the abnormality of the reader 250, and compares the pixels in read image data with the corresponding pixels in output image data, to detect a match or a mismatch.

[Configuration (2)]

Figure 3:
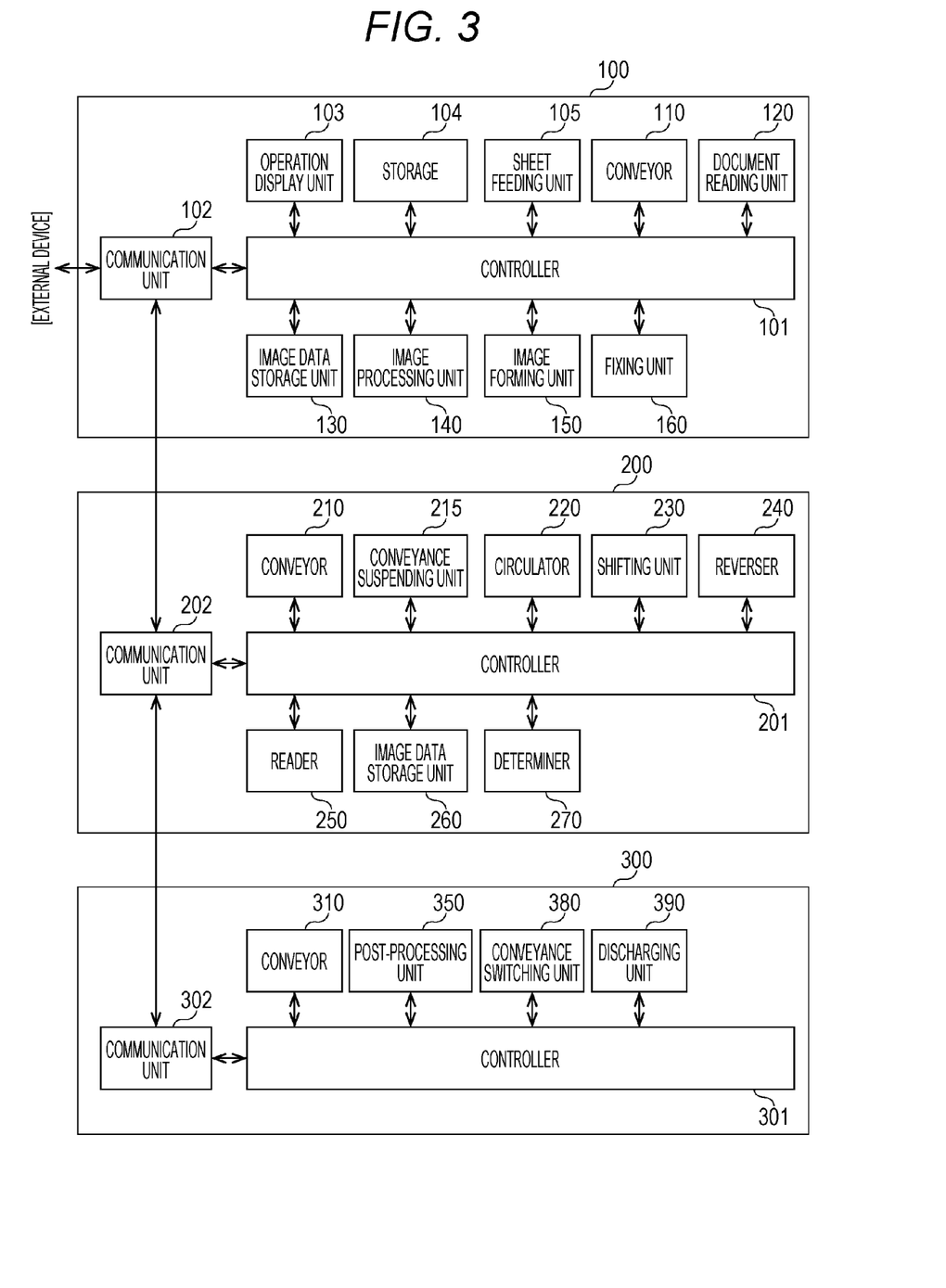
FIG. 3 is a diagram showing another configuration according to the embodiment of the present invention.
Figure 4:
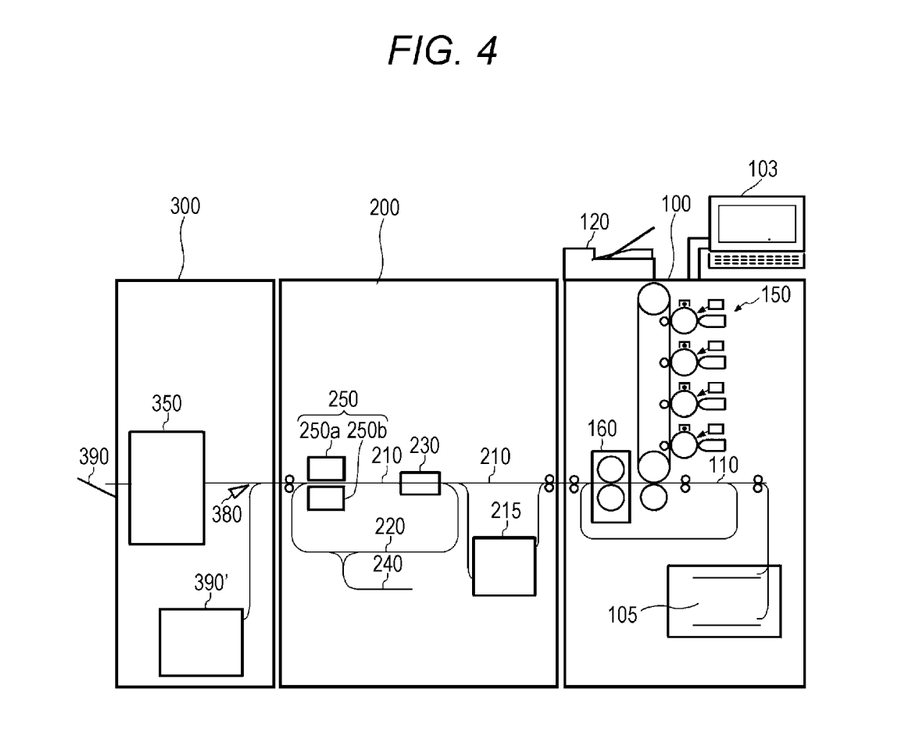
FIG. 4 is a diagram showing the configuration according to the embodiment of the present invention.

Referring now to FIGS. 3 and 4, a second example configuration of an image inspection apparatus and an image forming system is described in detail. It should be noted that explanation of the same components as those of the first example configuration will not be made below.

In this example, an image forming apparatus 100 an image inspection apparatus 200, and a post-processing apparatus 300 are connected in the direction of sheet conveyance, to form an image forming system. The conveyance switching unit 280 and the ejecting unit 290 in the image inspection apparatus 200 are eliminated. Instead, the post-processing apparatus 300 is designed to eject paper sheets.

In this example, the post-processing apparatus 300 includes: a controller 301; a communication unit 302; a conveyor 310 that conveys paper sheets to be subjected to post-processing; a post-processing unit 350 that performs various kinds of post-processing, such as cutting, on paper sheets; a conveyance switching unit 380 that switches sheet conveyance paths in accordance with a result of determination made in the image inspection apparatus 200; and an ejecting unit 390 that outputs normal images but does not output abnormal images.

[Supplementary Notes on the Configurations]

In the above described configurations (1) and (2), the shifting unit 230 is necessary in cases where an operation (3) that will be described later is performed. Therefore, in a case where the later described operation (3) is not performed, the shifting unit 230 may not be prepared. Meanwhile, the reverser 240 is necessary in cases where an operation (4) that will be described later is performed. Therefore, in a case where the later described operation (4) is not performed, the reverser 240 may not be prepared. In a case where the later described operation (4) is performed, the reader 250 is designed to perform two-side reading with the first-side reader 250a and the second-side reader 250b. Therefore, in a case where the later described operation (4) is not performed, the reader 250 performs one-side reading.

A match detected as a result of comparison performed at the determiner 270 is not necessarily a perfect match between all the pixels in output image data and all the pixels in read image data (or circulated read image data). For example, even if there is a small difference in thickness of characters or lines or in gray scale due to the image formation process, the image is regarded as normal in some cases. Therefore, a match is detected even when there is a small difference in the thickness or contour of characters or the lines of figures.

On the other hand, the determiner 270 preferably detects a mismatch when there are obviously different pixels that appear as independent points, such as smudges of toner or the like in an image, existence of missing portions in characters and an image due to insufficient adhesion of toner, and abnormality in image reading (an uncleaned sensor or optical system in the reader 250, for example).

Example Operation (1)

Figure 5:
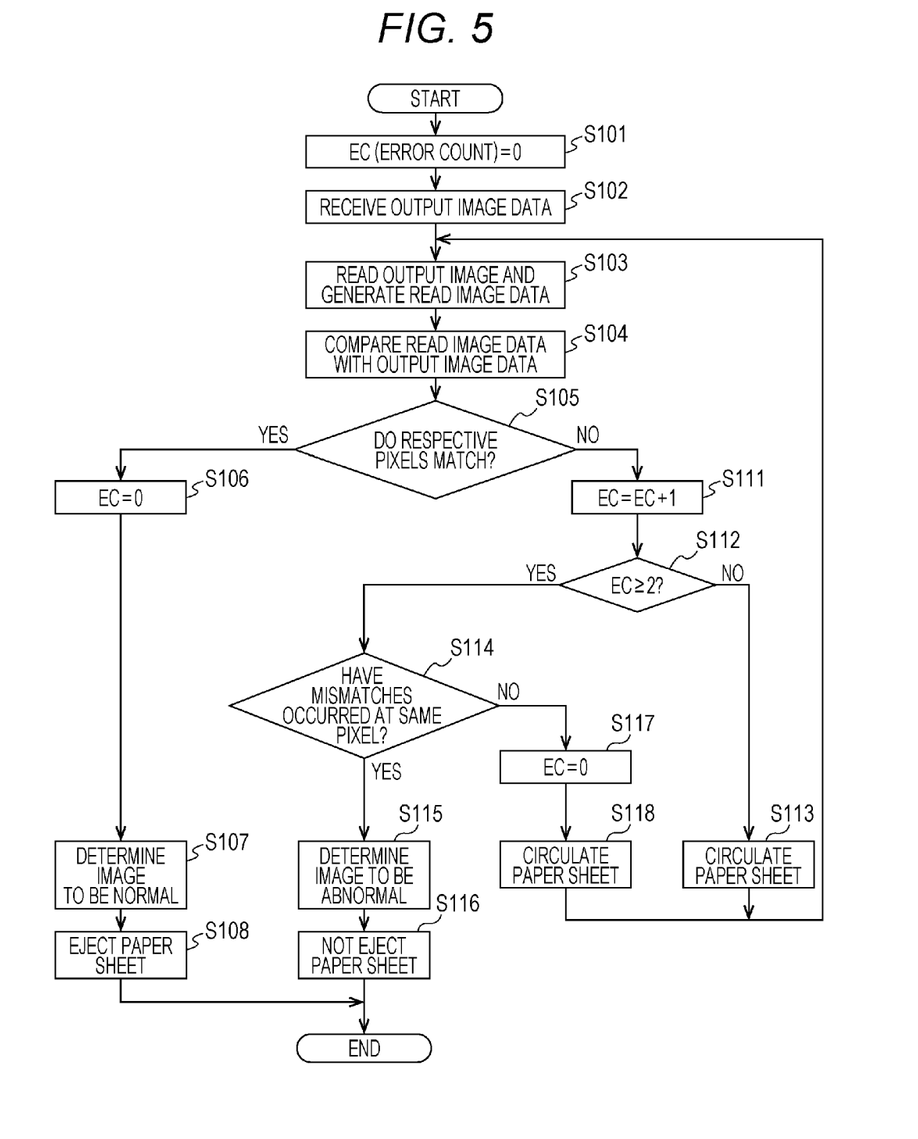
FIG. 5 is a flowchart showing an example operation according to the embodiment of the present invention.

Referring now to the flowchart in FIG. 5, an embodiment concerning an operation (operation procedures according to an image inspection method and an image inspection program) of the image forming system including the image inspection apparatus 200 is described as an operation (1) of this embodiment.

The flowchart in FIG. 5 shows the image inspection procedures to be carried out in the image inspection apparatus 200 for each paper sheet subjected to image formation performed in the image forming apparatus 100. It should be noted that, in the specific example described below, the image inspection apparatus 200 shown in FIGS. 1 and 2 performs control on image determination and ejection.

First, for a paper sheet subjected to image formation, the controller 201 initializes an error count (hereinafter referred to simply as "EC"; EC=0) that indicates an error count value detected by image inspection (step S101 in FIG. 5).

The controller 201 also receives the image data used for the image formation in the image forming apparatus 100 (the image data will be hereinafter referred to as the "output image data") from the image forming apparatus 100 via the communication unit 202, and stores the output image data into the image data storage unit 260 (step S102 in FIG. 5). It should be noted that the image forming apparatus 100 transmits output image data to the image inspection apparatus 200 every time the image forming unit 150 performs image formation on a paper sheet.

The controller 201 receives a paper sheet output from the image forming apparatus 100, and performs control so that the paper sheet is conveyed at a constant speed by the conveyor 210. The controller 201 further performs control so that the image on the paper sheet is read by the reader 250 during the conveyance. The reader 250 reads the image on the paper sheet being conveyed at the constant speed, and generates read image data (step S103 in FIG. 5). The read image data is stored into the image data storage unit 260 as necessary.

Receiving an instruction from the controller 201, the determiner 270 compares the pixels in the read image data with the corresponding pixels in the output image data, and determines whether the pixels match (step S104 in FIG. 5). The determiner 270 may also perform image processing, as necessary, to enlarge or reduce a data size so that the two image data sizes become the same.

If the determiner 270 determines that the respective pixels match as a result of the comparison between the pixels (YES in step S105 in FIG. 5), the controller 201 sets the EC at 0 (EC=0) (step S106 in FIG. 5). The determiner 270 then determines that the image formed on the paper sheet is normal, and notifies the controller 201 of the result of the determination (step S107 in FIG. 5). Receiving the notification of image normality from the determiner 270, the controller 201 controls the conveyance switching unit 280 to switch the path to the one leading to the ejecting unit 290, so that the paper sheet is ejected from the ejecting unit 290 (step S108 in FIG. 5).

If a mismatch is detected from any of the pixels as a result of the comparison between the pixels by the determiner 270 (NO in step S105 in FIG. 5), on the other hand, the controller 201 increments the error count by 1 (EC=EC+1) (step S111 in FIG. 5). Here, the determiner 270 stores the address of the pixel from which the mismatch is detected.

Figure 6A:
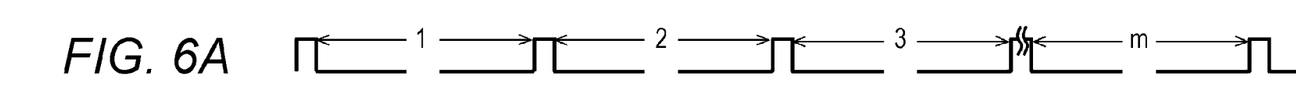
FIGS. 6A through 6C are charts for explaining the example operation according to the embodiment of the present invention.
Figure 6B:
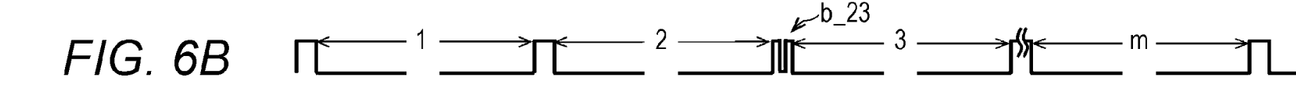
Figure 6C:
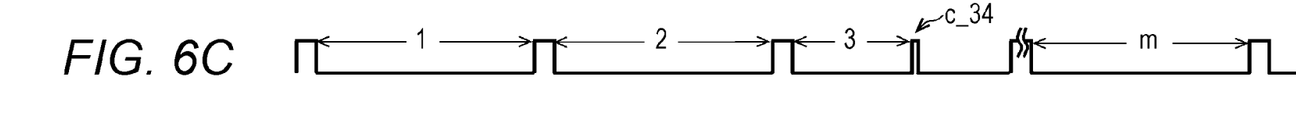

The determiner 270 can also sense abnormality of read image data from a synchronization signal or a valid region signal included in the read image data generated by the reader 250. FIG. 6A shows read image data at a normal time. In the read image data, each H-level portion indicates a horizontal synchronization signal, and each L-level portion indicates a horizontal valid region signal. In FIG. 6B, reference numeral b23 indicates noise appearing in a horizontal synchronization signal. In FIG. 6C, reference numeral c34 indicates noise appearing in a horizontal valid region signal. In this case, each portion having a larger variation in signal width than those in the other signals can be determined to have noise. If the determiner 270 senses such abnormality, the error count EC is incremented as in the above described case where a mismatch is detected between pixels as a result of comparison (NO in step S105, and S111 in FIG. 5).

The controller 201 determines whether the error count EC incremented as above is not smaller than 2 (EC≥2) (step S112 in FIG. 5). If the EC is 1 (EC=1) (NO in step S112 in FIG. 5), a mismatch is detected as a result of comparison between the pixels in the output image data and the pixels in the read image data in the first-time reading performed on the paper sheet. That is, at this point of operation, the cause of the mismatch detected as a result of the comparison between the pixels has not yet been determined to be abnormality of the image, abnormality of the reader, or adverse influence of noise.

Therefore, the controller 201 controls the circulator 220 to circulate the paper sheet in the circulator 220 and return the paper sheet to the reader 250 (step S113 in FIG. 5). As a result, read image data generation in the reader 250 reading the paper sheet (step S103 in FIG. 5), and determination as to whether the pixels in the read image data match the corresponding pixels in the output image data through comparison in the determiner 270 (step S104 in FIG. 5) are again performed.

If the determiner 270 determines that the respective pixels match as a result of comparison between the pixels in second-time or later circulated read image data generated through circulation and the pixels in the output image data (YES in step S105 in FIG. 5), the controller 201 sets the EC at 0 (EC=0) (step S106 in FIG. 5). The determiner 270 then determines that the image formed on the paper sheet is normal, and notifies the controller 201 of the result of the determination (step S107 in FIG. 5). Receiving the notification of image normality from the determiner 270, the controller 201 controls the conveyance switching unit 280 to switch the path to the one leading to the ejecting unit 290, so that the paper sheet is ejected from the ejecting unit 290 (step S108 in FIG. 5).

If a mismatch is again detected by the determiner 270 from any of the pixels as a result of comparison between the pixels in the second-time or later circulated read image data generated through circulation and the pixels in the output image data (NO in step S105 in FIG. 5), on the other hand, the controller 201 increments the error count by 1 (EC=EC+1) (step S111 in FIG. 5). Here, the determiner 270 stores the address of the pixel from which the mismatch is detected.

If a mismatch is detected between the circulated read image data generated through the second-time or later circulation and the output image data, the controller 201 makes determination on the error count EC (step S112 in FIG. 5), and determines the EC not to be smaller than 2 (EC≥2) (YES in step S112 in FIG. 5).

Here, the controller 201 instructs the determiner 270 to determine whether the mismatch detected as a result of comparison after circulation has occurred at the same pixel from which the mismatch before the circulation has been detected.

That is, in a case where a mismatch is detected as a result of comparison between the read image data generated through the first-time reading and the output image data, and a mismatch is detected as a result of comparison between the circulated read image data generated through the second-time reading and the output image data, if these mismatches have occurred at the same pixel (YES in step S114 in FIG. 5), the determiner 270 determines the image to be abnormal, and notifies the controller 201 of the determination result (step S115 in FIG. 5). Receiving the notification of image abnormality from the determiner 270, the controller 201 controls the conveyance switching unit 280 to switch the path to the one leading to an accumulating unit 290', so that the paper sheet is not ejected (step S116 in FIG. 5).

In a case where a mismatch is detected as a result of comparison between the read image data generated through the first-time reading and the output image data, and a mismatch is detected as a result of comparison between the circulated read image data generated through the second-time reading and the output image data, if these mismatches have occurred at different pixels (NO in step S114 in FIG. 5), on the other hand, the determiner 270 notifies the controller 201 that the mismatches have occurred at different pixels. In this case, the mismatches at different pixels are probably due to electrical noise or the like. Therefore, the controller 201 resets the error count EC (EC=0) (step S117 in FIG. 5), and controls the circulator 220 to circulate the paper sheet in the circulator 220 and return the paper sheet to the reader 250 (step S118 in FIG. 5). In this case, electrical noise or the like does not appear in the next circulated read image data (step S103 in FIG. 5), and, as a result of pixel comparison (step S104 in FIG. 5), the respective pixels in the circulated read image data might match the respective pixels in the output image data in the determiner 270 (YES in step S105 in FIG. 5).

As described above, in a case where a mismatch is detected by the determiner 270, the circulated paper sheet is read by the reader 250, and the circulated read image data is compared with the output image data. In this manner, a check is made to determine whether the image is normal. Thus, it is possible to determine whether an image formed on a paper sheet output from the image forming apparatus 100 is normal, with a higher degree of accuracy than in conventional cases.

Example Operation (2)

Figure 7:
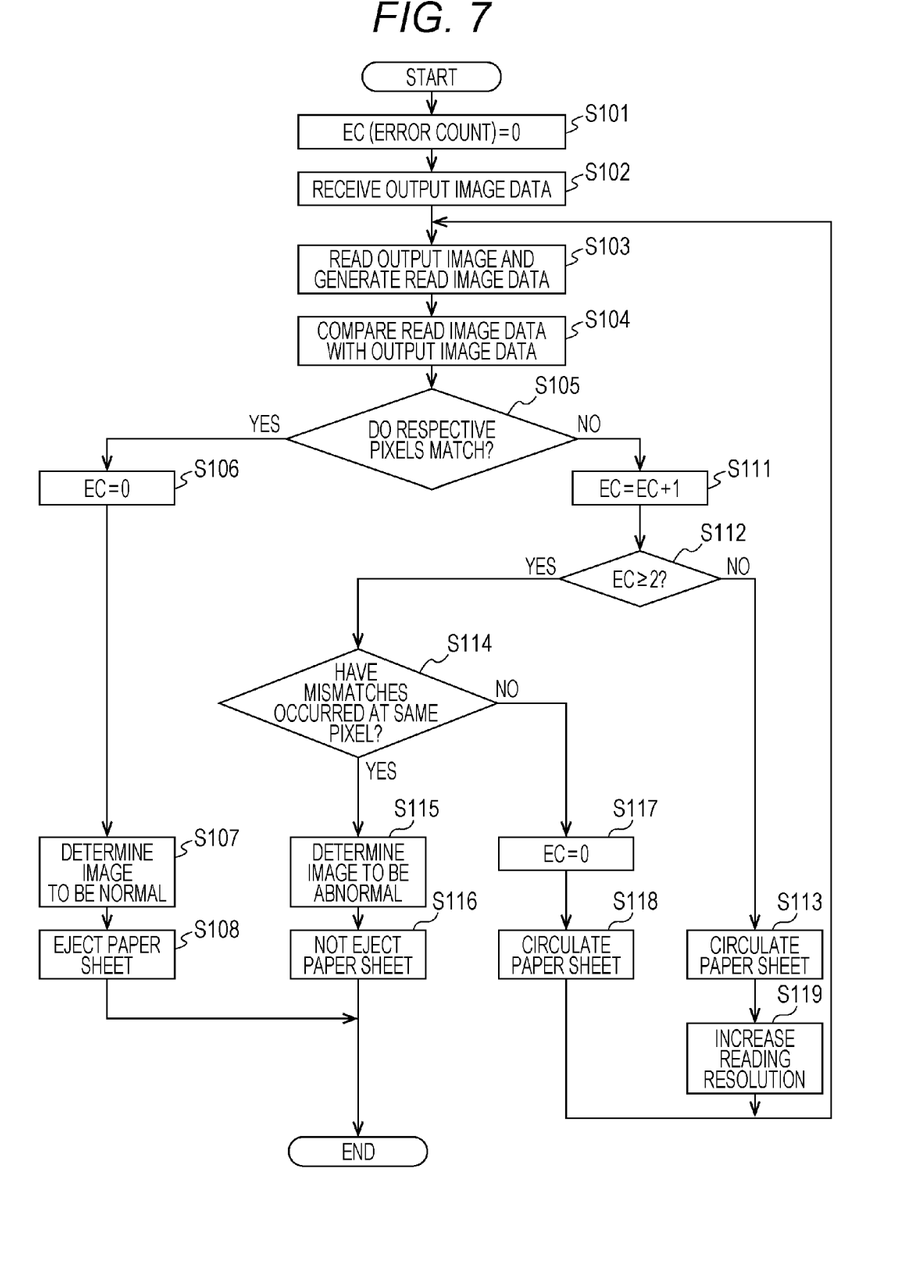
FIG. 7 is a flowchart showing another example operation according to the embodiment of the present invention.

Referring now to the flowchart in FIG. 7, an embodiment concerning an operation (operation procedures according to an image inspection method and an image inspection program) of the image forming system including the image inspection apparatus 200 is described as an operation (2) of this embodiment. It should be noted that explanation of the same steps as those of the operation (1) will not be made below.

The flowchart in FIG. 7 shows the image inspection procedures to be carried out in the image inspection apparatus 200 for each paper sheet subjected to image formation performed in the image forming apparatus 100. It should be noted that, in the specific example described below, the image inspection apparatus 200 shown in FIGS. 1 and 2 performs control on image determination and ejection.

The controller 201 determines whether the error count EC incremented as described above (step S111 in FIG. 7) is not smaller than 2 (EC≥2) (step S112 in FIG. 7). If the EC is 1 (EC=1) (NO in step S112 in FIG. 7), a mismatch is detected as a result of comparison between the pixels in the output image data and the pixels in the read image data in the first-time reading performed on the paper sheet. That is, at this point of operation, the cause of the mismatch detected as a result of the comparison between the pixels has not yet been determined to be abnormality of the image, abnormality of the reader, or adverse influence of noise.

Therefore, the controller 201 controls the circulator 220 to circulate the paper sheet in the circulator 220 and return the paper sheet to the reader 250 (step S113 in FIG. 7). The controller 201 also lowers the speed of the conveyance being performed by the conveyor 210, to increase the reading resolution at the reader 250 in the direction of conveyance (step S119 in FIG. 7). For example, if the speed of the conveyance being performed by the conveyor 210 is halved, the reading resolution at the reader 250 in reading the generated read image data (second-time or later step S103 after circulation in FIG. 7) is doubled in the direction of conveyance.

In this case, the determiner 270 increases the image size of the output image data by duplicating pixels in the sub scanning direction (=the direction of conveyance), and then again determines whether the pixels in the read image data match the corresponding pixels in the output image data through comparison between the pixels (step S104 in FIG. 7).

Electrical noise appears at random, but smudges in an image are detected with a resolution twice as high. Thus, the comparison accuracy is increased. That is, comparison between circulated read image data and output image data can be performed with a high degree of accuracy, and a check can be made to accurately determine whether an image formed on a paper sheet output from the image forming apparatus is normal.

It should be noted that, in controlling the conveyance speed to increase the resolution as above, the conveyance speed is not necessarily halved, but any appropriate resolution (conveyance speed) can be selected.

Also, when the conveyance speed is lowered in the image inspection apparatus 200, the timing to inspect the next paper sheet to be sent from the image forming apparatus 100 might overlap the timing to inspect the current paper sheet. To counter this, the controller 201 temporarily stores the yet-to-be-read paper sheet into the conveyance suspending unit 215, and suspends the conveyance.

Example Operation (3)

Figure 8:
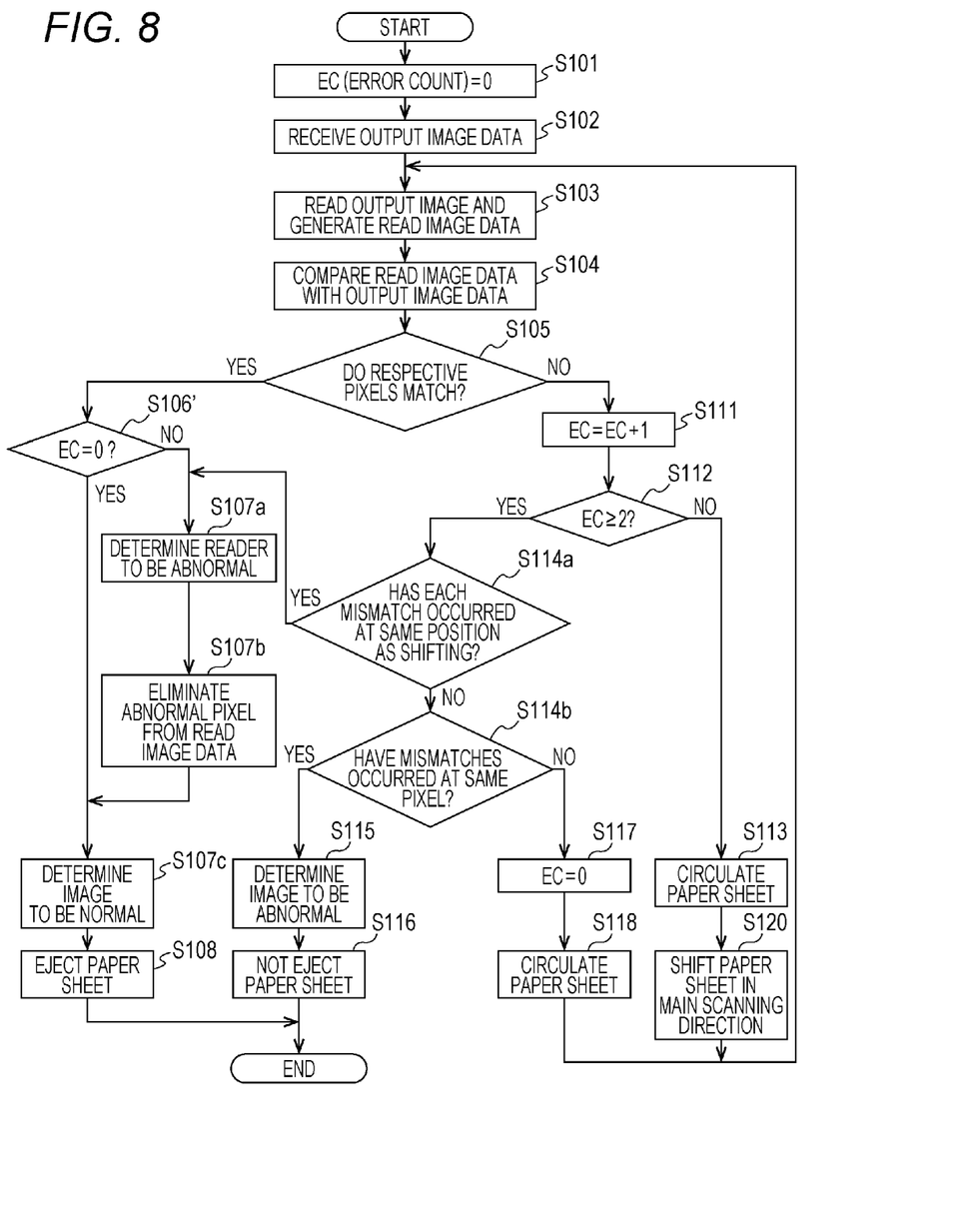
FIG. 8 is a flowchart showing yet another example operation according to the embodiment of the present invention.

Referring now to the flowchart in FIG. 8, an embodiment concerning an operation (operation procedures according to an image inspection method and an image inspection program) of the image forming system including the image inspection apparatus 200 is described as an operation (3) of this embodiment. It should be noted that explanation of the same steps as those of the operation (1) will not be made below.

The flowchart in FIG. 8 shows the image inspection procedures to be carried out in the image inspection apparatus 200 for each paper sheet subjected to image formation performed in the image forming apparatus 100. It should be noted that, in the specific example described below, the image inspection apparatus 200 shown in FIGS. 1 and 2 performs control on image determination and ejection.

The controller 201 determines whether the error count EC incremented as described above (step S111 in FIG. 8) is not smaller than 2 (EC≥2) (step S112 in FIG. 8). If the EC is 1 (EC=1) (NO in step S112 in FIG. 8), a mismatch is detected as a result of comparison between the pixels in the output image data and the pixels in the read image data in the first-time reading performed on the paper sheet. That is, at this point of operation, the cause of the mismatch detected as a result of the comparison between the pixels has not yet been determined to be abnormality of the image, abnormality of the reader, or adverse influence of noise.

Therefore, the controller 201 controls the circulator 220 to circulate the paper sheet in the circulator 220 and return the paper sheet to the reader 250 (step S113 in FIG. 8). The controller 201 also issues an instruction to the shifting unit 230, so that the same paper sheet is moved by different amounts in a direction (main scanning direction) perpendicular to the conveying direction (sub scanning direction) in conveyance operations performed by the conveyor 210 to convey the paper sheet before and after circulation performed by the circulator 220 (step S120 in FIG. 8).

The reader 250 then reads the shifted paper sheet, and generates circulated read image data (step S103 in FIG. 8). In this case, the determiner 270 performs comparison and determines whether the pixels in the output image data match the corresponding pixels in the circulated read image data after the shifting (step S104 in FIG. 8).

If the determiner 270 determines that the respective pixels in the output image data match the respective pixels in the circulated read image data as a result of the comparison between the pixels (YES in step S105 in FIG. 8), the controller 201 determines whether the EC is 0 (EC=0) (step S106' in FIG. 8).

If the EC is 0 (EC=0) (YES in step S106' in FIG. 8), the read image data generated through the first-time reading matches the output image data. The determiner 270 then determines that the image formed on the paper sheet is normal, and notifies the controller 201 of the determination result (step S107c in FIG. 8). Receiving the notification of image normality from the determiner 270, the controller 201 controls the conveyance switching unit 280 to switch the path to the one leading to the ejecting unit 290, so that the paper sheet is ejected from the ejecting unit 290 (step S108 in FIG. 8).

If the EC is not 0 (EC≠0) (NO in step S106' in FIG. 8), on the other hand, the read image data generated through the first-time reading does not match the output image data, and the circulated read image data generated through circulated reading involving the shifting matches the output image data. In this case, it is assumed that normal circulated read image data is obtained, because any smudged region of the reader 250 is not used in the reading, by virtue of the shifting (step S120 in FIG. 8). Therefore, the determiner 270 determines that the reader 250 has abnormality, and notifies the controller 201 of the determination result (step S107a in FIG. 8). Since the pixel having abnormality in the first-time read image data is assumed to be a smudged region, the determiner 270 arranges a setting to eliminate the pixel from the next comparison object (step S107b in FIG. 8). The determiner 270 also determines that the image formed on the paper sheet is normal though the reader 250 has abnormality, and then notifies the controller 201 of the determination result (step S107c in FIG. 8). Receiving the notification of image normality from the determiner 270, the controller 201 controls the conveyance switching unit 280 to switch the path to the one leading to the ejecting unit 290, so that the paper sheet is ejected from the ejecting unit 290 (step S108 in FIG. 8).

The controller 201 also determines whether the error count EC incremented as described above (step S111 in FIG. 8) is not smaller than 2. If the EC is not smaller than 2 (EC≥2) (YES in step S112 in FIG. 8), a mismatch is detected as a result of comparison between the pixels read in the first-time reading and the pixels read in the second-time or later reading performed on the paper sheet. That is, in a case where a mismatch is detected as a result of comparison between the read image data and the output image data, and a mismatch is detected as a result of comparison between the circulated read image data generated through circulation involving shifting and the output image data (YES in step S112 in FIG. 8), if the respective mismatches have occurred at the pixels in the positions equivalent to the shifting performed on the paper sheet by the shifting unit 230 (or in the position of the same light receiving element in the imaging element of the reader 250) (YES in step S114a in FIG. 8), the determiner 270 determines that the mismatches are due to a smudged region of the reader 250.

Therefore, the determiner 270 determines that the reader 250 has abnormality, and notifies the controller 201 of the determination result (step S107a in FIG. 8). Since the pixel having abnormality in the read image data and in the circulated read image data generated through circulation involving the shifting is assumed to be a smudged region, the determiner 270 arranges a setting to eliminate the pixel from the next read image data (step S107b in FIG. 8). The determiner 270 also determines that the image formed on the paper sheet is normal though the reader 250 has abnormality, and then notifies the controller 201 of the determination result (step S107c in FIG. 8). Receiving the notification of image normality from the determiner 270, the controller 201 controls the conveyance switching unit 280 to switch the path to the one leading to the ejecting unit 290, so that the paper sheet is ejected from the ejecting unit 290 (step S108 in FIG. 8).

The controller 201 determines whether the error count EC incremented as described above (step S111 in FIG. 8) is not smaller than 2. If the EC is not smaller than 2 (EC≥2) (YES in step S112 in FIG. 8), a mismatch is detected as a result of comparison between the read image data generated through the first-time reading and the output image data, and a mismatch is detected as a result of comparison between the circulated read image data generated through second-time or later reading involving shifting and the output image data. In this case, if each of the mismatches has occurred at the pixel in a different position from the shifting performed on the paper sheet by the shifting unit 230 (NO in step S114a in FIG. 8), and the respective mismatches have occurred at the same pixel (YES in step S114b in FIG. 8), the determiner 270 determines the image to be abnormal, and notifies the controller 201 of the determination result (step S115 in FIG. 8). Receiving the notification of image abnormality from the determiner 270, the controller 201 controls the conveyance switching unit 280 to switch the path to the one leading to the accumulating unit 290', so that the paper sheet is not ejected (step S116 in FIG. 8).

In a case where a mismatch is detected as a result of comparison between the read image data generated through the first-time reading and the output image data, and a mismatch is detected as a result of comparison between the circulated read image data generated through the second-time reading and the output image data, if each of the mismatches has occurred at a pixel in a different position from the shifting performed on the paper sheet by the shifting unit 230 (NO in step S114a in FIG. 8), and if the respective mismatches have occurred at different pixels (NO in step S114b in FIG. 8), the determiner 270 notifies the controller 201 that the mismatches have occurred at different pixels. In this case, the mismatches at different pixels are probably due to electrical noise or the like. Therefore, the controller 201 resets the error count EC (EC=0) (step S117 in FIG. 8), and controls the circulator 220 to circulate the paper sheet in the circulator 220 and return the paper sheet to the reader 250 (step S118 in FIG. 8).

It should be noted that the shifting in the main scanning direction by the shifting unit 230 in step S120 is preferably shifting by a different amount every time the paper sheet is circulated, so as to identify the cause of a mismatch at a pixel.

As described above, in conveyance operations performed by the conveyor 210 to convey the same paper sheet before and after circulation by the circulator 220, the paper sheet is moved by different amounts in a direction perpendicular to the sheet conveyance by the shifting unit 230, so that abnormality of the reader 250 (step S107a in FIG. 8), abnormality of an image (step S115 in FIG. 8), and abnormality due to electrical noise (NO in step S114a, NO in step S114b, and step S117 in FIG. 8) can be distinguished from one another. Thus, it is possible to accurately determine whether an image formed on a paper sheet output from the image forming apparatus 100 is normal.

Although not shown in the flowchart in FIG. 8, when the paper sheet is circulated and shifted, and is then returned to the reader 250 (steps S113 and S120 in FIG. 8), the controller 201 may increase the resolution by changing the conveyance speed as described in the operation (2), and thus, increase the comparison accuracy.

Example Operation (4)

Figure 9:
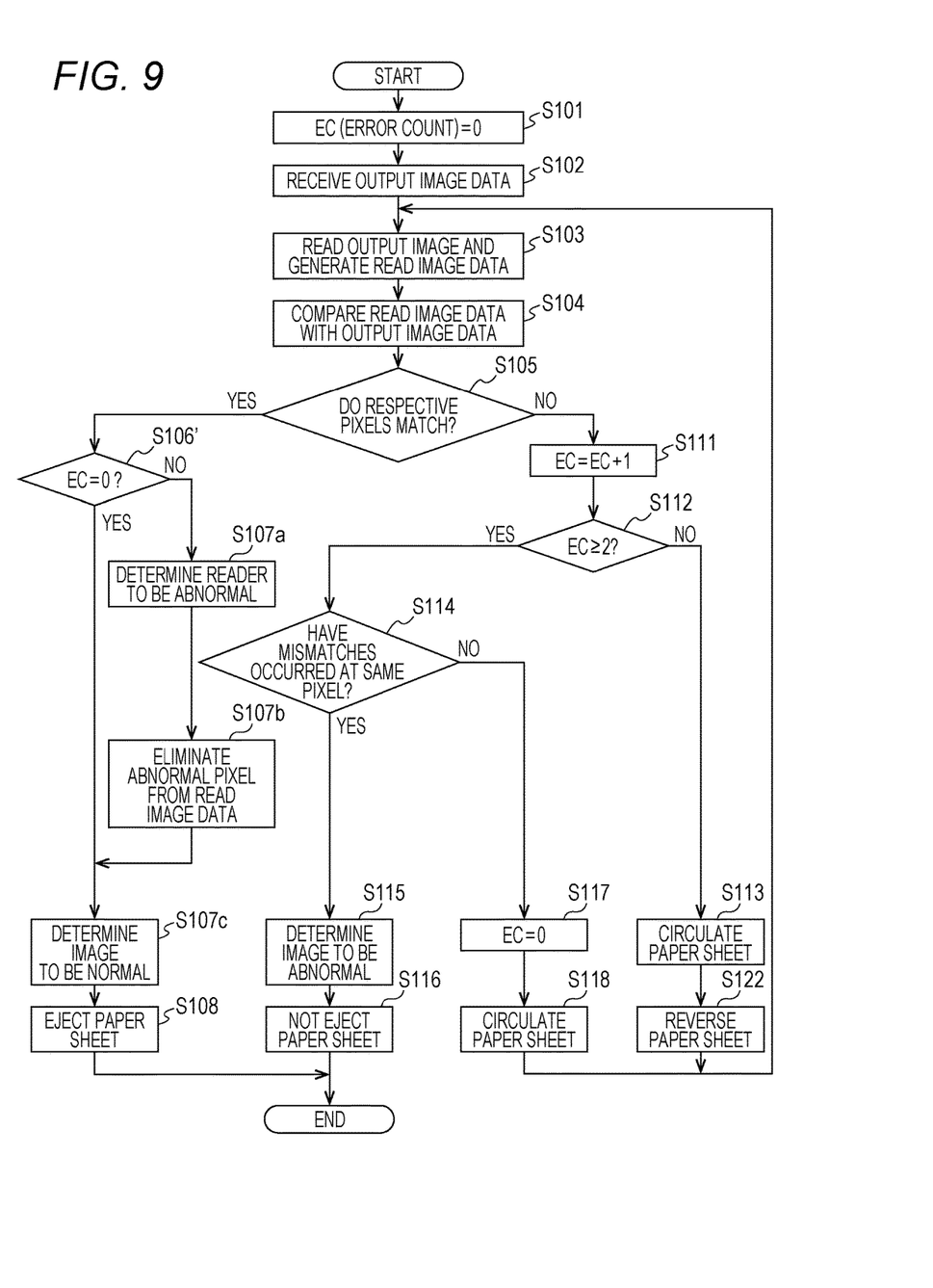
FIG. 9 is a flowchart showing still another example operation according to the embodiment of the present invention.

Referring now to the flowchart in FIG. 9, an embodiment concerning an operation (operation procedures according to an image inspection method and an image inspection program) of the image forming system including the image inspection apparatus 200 is described as an operation (4) of this embodiment. It should be noted that explanation of the same steps as those of the operation (1) will not be made below.

The flowchart in FIG. 9 shows the image inspection procedures to be carried out in the image inspection apparatus 200 for each paper sheet subjected to image formation performed in the image forming apparatus 100. It should be noted that, in the specific example described below, the image inspection apparatus 200 shown in FIGS. 1 and 2 performs control on image determination and ejection.

The controller 201 determines whether the error count EC incremented as described above (step S111 in FIG. 9) is not smaller than 2 (EC≥2) (step S112 in FIG. 9). If the EC is 1 (EC=1) (NO in step S112 in FIG. 9), a mismatch is detected as a result of comparison between the pixels in the output image data and the pixels in the read image data in the first-time reading performed on the paper sheet. That is, at this point of operation, the cause of the mismatch detected as a result of the comparison between the pixels has not yet been determined to be abnormality of the image, abnormality of the reader, or adverse influence of noise.

Therefore, the controller 201 controls the circulator 220 to circulate the paper sheet in the circulator 220 and return the paper sheet to the reader 250 (step S113 in FIG. 9). The controller 201 also instructs the reverser 240 to reverse the paper sheet in conveyance operations performed by the conveyor 210 to convey the paper sheet circulated by the circulator 220 (step S122 in FIG. 9). It is only required that a paper sheet is reversed before or after circulation. To achieve a higher processing speed, however, it is normally preferable to perform control so that the paper sheet is not reversed in the first-time regular conveyance, but the paper sheet is reversed in the second-time conveyance through circulation, for example.

The reader 250 then reads the reversed paper sheet, and generates circulated read image data (step S103 in FIG. 9). Here, the first-side reader 250a performs the first-time reading, and the second-side reader 250b performs the second-time reading after the reversal. In this case, the determiner 270 performs comparison and determines whether the pixels in the output image data match the corresponding pixels in the circulated read image data after the reversal (step S104 in FIG. 9).

If the determiner 270 determines that the respective pixels in the output image data match the respective pixels in the circulated read image data as a result of the comparison between the pixels (YES in step S105 in FIG. 9), the controller 201 determines whether the EC is 0 (EC=0) (step S106' in FIG. 9).

If the EC is 0 (EC=0) (YES in step S106' in FIG. 9), the read image data generated through the first-time reading performed by the first-side reader 250a matches the output image data. The determiner 270 then determines that the image formed on the paper sheet is normal, and notifies the controller 201 of the determination result (step S107c in FIG. 9). Receiving the notification of image normality from the determiner 270, the controller 201 controls the conveyance switching unit 280 to switch the path to the one leading to the ejecting unit 290, so that the paper sheet is ejected from the ejecting unit 290 (step S108 in FIG. 9).

If the EC is not 0 (EC≠0) (NO in step S106' in FIG. 9), on the other hand, the read image data generated through the first-time reading performed by the first-side reader 250a does not match the output image data, and the circulated read image data generated through reading performed on the reversed sheet by the second-side reader 250b matches the output image data. In this case, the second-side reader 250b used after the reversal (step S122 in FIG. 9) is assumed to be normal, but the first-side reader 250a used before the reversal is assumed to be abnormal.

Therefore, the determiner 270 determines that the first-side reader 250a has abnormality, and notifies the controller 201 of the determination result (step S107a in FIG. 9). Since the pixel having abnormality in the first-time read image data is assumed to be a smudged region, the determiner 270 arranges a setting to eliminate the pixel from the next comparison object (step S107b in FIG. 9).

The determiner 270 also determines that the image formed on the paper sheet is normal though the first-side reader 250a has abnormality, and then notifies the controller 201 of the determination result (step S107c in FIG. 9). Receiving the notification of image normality from the determiner 270, the controller 201 controls the conveyance switching unit 280 to switch the path to the one leading to the ejecting unit 290, so that the paper sheet is ejected from the ejecting unit 290 (step S108 in FIG. 9).

As described above, in one of the conveyance operations performed by the conveyor 210 to convey the same paper sheet before and after circulation by the circulator 220, the paper sheet is reversed by the reverser 240, so that abnormality of the reader 250 (step S107a in FIG. 9), abnormality of an image (step S115 in FIG. 9), and abnormality due to electrical noise (NO in step S114, and step S117 in FIG. 9) can be distinguished from one another. Thus, it is possible to accurately determine whether an image formed on a paper sheet output from the image forming apparatus 100 is normal.

Although not shown in the flowchart in FIG. 9, when the paper sheet is circulated and reversed, and is then returned to the reader 250 (steps S113 and S122 in FIG. 9), the controller 201 may increase the resolution by changing the conveyance speed as described in the operation (2), and thus, increase the comparison accuracy.

Example Operation (5)

Figure 10:
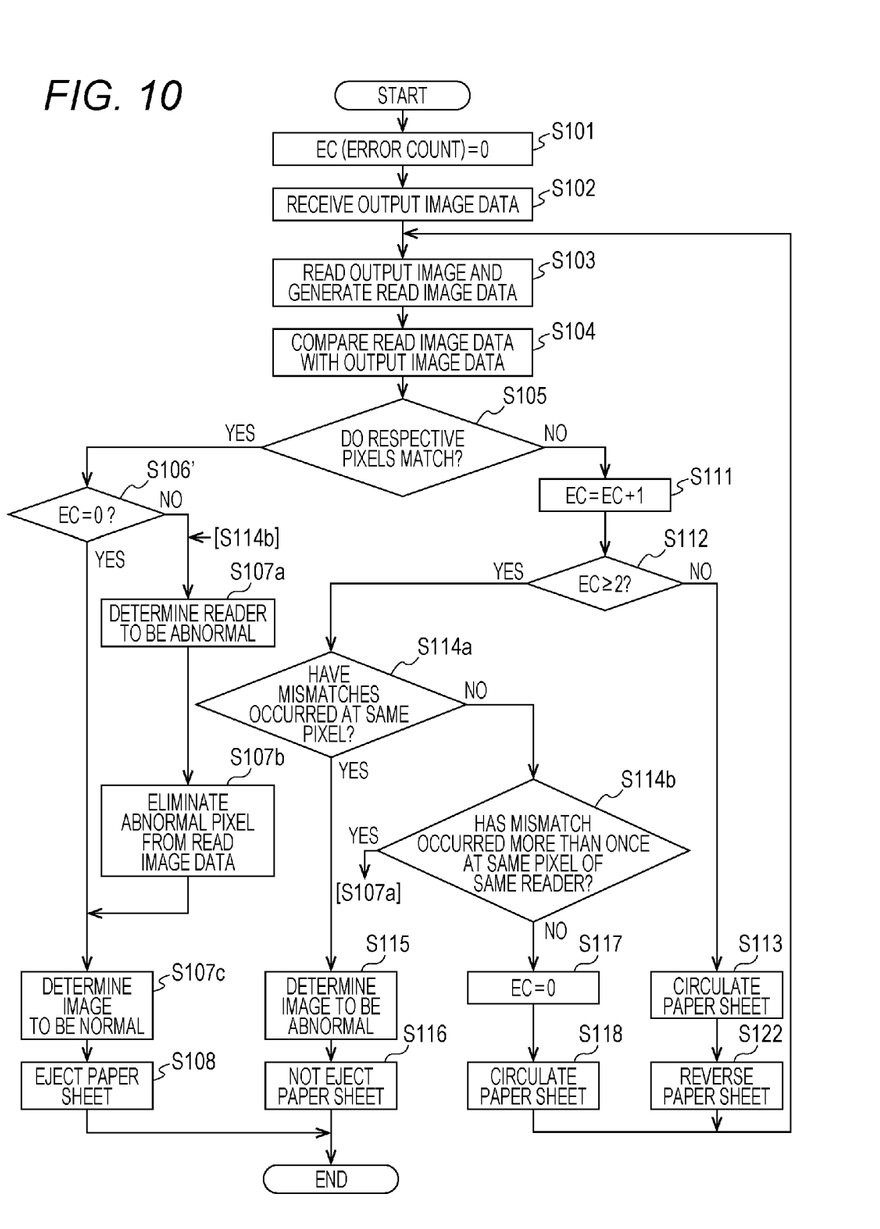
FIG. 10 is a flowchart showing yet another example operation according to the embodiment of the present invention.

Referring now to the flowchart in FIG. 10, an embodiment concerning an operation (operation procedures according to an image inspection method and an image inspection program) of the image forming system including the image inspection apparatus 200 is described as an operation (5) of this embodiment. Since the operation (5) is an improvement of the operation (4), explanation of the same steps as those of the operation (4) will not be made below.

First, in a case where a mismatch is detected as a result of comparison between the read image data generated through the first-time reading and the output image data, and where a mismatch is detected as a result of comparison between the circulated read image data generated through the second-time reading and the output image data, and the respective mismatches have occurred at different pixels (NO in step S114a in FIG. 10), the mismatches at the different pixels are assumed to be due to electrical noise or the like. Therefore, the controller 201 resets the error count EC (EC=0) (step S117 in FIG. 10), and controls the circulator 220 to circulate the paper sheet in the circulator 220 and return the paper sheet to the reader 250 (step S118 in FIG. 10).

In this case, if electrical noise or the like is not the cause, but abnormality such as a smudged region exists in the first-side reader 250a while abnormality such as a smudged region also exists in the second-side reader 250b, the determination as to whether the mismatches have occurred at the same pixel (NO in step S114a in FIG. 10), and the EC resetting and the sheet circulation (steps S117 and S118 in FIG. 10) are repetitively performed.

Therefore, in a case where the result of the determination as to whether the mismatches have occurred at the same pixel is negative (NO in step S114a in FIG. 10), the determiner 270 determines whether a mismatch detected as a result of comparison between read image data and the output image data has occurred more than once at a particular pixel, and whether a mismatch detected as a result of comparison between circulated read image data generated through reading after a reversal and the output image data has occurred more than once at another particular pixel (step S114b in FIG. 10).

If this condition is satisfied (YES in step S114b in FIG. 10), the determiner 270 determines that both the first-side reader 250a and the second-side reader 250b have abnormality, and notifies the controller 201 of the determination result (step S107a in FIG. 10). Since the pixel having abnormality in the read image data generated by the first-side reader 250a is assumed to be a smudged region, and the pixel having abnormality in the read image data generated by the second-side reader 250b is also assumed to be a smudged region, the determiner 270 arranges a setting to eliminate the pixels from the next comparison object (step S107b in FIG. 10).

As described above, in one of the conveyance operations performed by the conveyor 210 to convey the same paper sheet before and after circulation by the circulator 220, the paper sheet is reversed by the reverser 240, so that abnormality of the first-side reader 250a (NO in step S106', and step S107a in FIG. 10), abnormality of the second-side reader 250b (NO in step S114b, and step S107a in FIG. 10), abnormality of an image (step S115 in FIG. 10), and abnormality due to electrical noise (NO in step S114a, NO in step S114b, and S117 in FIG. 10) can be distinguished from one another. Thus, it is possible to accurately determine whether an image formed on a paper sheet output from the image forming apparatus 100 is normal.

Example Operation (6)

The techniques used in the above described operations (1) through (5) may be combined. For example, in reading a paper sheet, circulation and shifting, circulation and a reversal, and circulation and shifting are performed in this order, so that the paper sheet can be circulated to pass through both the first-side reader 250a and the second-side reader 250b while being shifted. As a result, it is possible to accurately determine whether an image formed on a paper sheet output from the image forming apparatus 100 is normal, and further accurately determine whether the first-side reader 250a and the second-side reader 250b are normal. In this case, it is also possible to increase the resolution by changing the conveyance speed as described in the operation (2), and thus, increase the comparison accuracy.

[Modification (1)]

In the above described embodiment, the accumulating unit 290' shown in FIG. 2 and the accumulating unit 390' shown in FIG. 4 may not be a box-like component that stores paper sheets therein, but may be a sheet catch tray that is prepared separately from a conventional ejecting unit, and catches ejected paper sheets.

[Modification (2)]

In the above described embodiment, the accumulating unit 290' shown in FIG. 2 and the accumulating unit 390' shown in FIG. 4 may not be prepared. Instead, a paper sheet having an abnormal image formed thereon is shifted or rotated more greatly than normal, and is then ejected by the ejecting unit 290 or the ejecting unit 390, so that such a paper sheet can be distinguished from paper sheets each having a normal image formed thereon.

[Modification (3)]

Although the image forming apparatus 100 and the image inspection apparatus 200 are connected to each other in FIGS. 1 through 4, the image forming apparatus 100 and the image inspection apparatus 200 are not necessarily connected. For example, the image inspection apparatus 200 may be separated from the image forming apparatus 100, but include a sheet feeding unit on which one or more paper sheets each having an image formed thereon are placed, and can receive output image data via a network. In this case, the above described image inspection can be conducted, as long as the order of the paper sheets placed on the sheet feeding unit is the same as the order of the output image data to be received via a network.

Although embodiments of the present invention have been described and illustrated in detail, it is clearly understood that the same is by way of illustration and example only and not limitation, the scope of the present invention should be interpreted by terms of the appended claims

What is claimed is:

1. An image inspection apparatus comprising:
   a storage that stores output image data used in forming an image on a paper sheet;
   a conveyor that conveys the paper sheet on which the image is formed;
   a reader that reads the image formed on the paper sheet during conveyance being performed by the conveyor, and generates read image data;
   a determiner that compares pixels in the read image data with corresponding pixels in the output image data, and determines whether the read image data matches the output image data;
   a circulator that circulates the paper sheet from which the image has been read by the reader, and returns the paper sheet to the reader; and
   a controller that controls the circulator to circulate the paper sheet and return the paper sheet to the reader when a mismatch is detected by the determiner,
   wherein
   the reader generates circulated read image data when the paper sheet is circulated and conveyed to the reader,
   when a match is detected as a result of comparison between the read image data and the output image data, the determiner determines that the image formed on the paper sheet is normal,
   when a match is detected as a result of comparison between the circulated read image data and the output image data, the determiner determines that the image formed on the paper sheet is normal, and
   when a mismatch is detected as a result of comparison between the circulated read image data and the output image data, the determiner determines that the image formed on the paper sheet is abnormal.

2. The image inspection apparatus according to claim 1, wherein
   the determiner senses abnormality of the read image data from one of a synchronization signal and a valid region signal included in the read image data generated by the reader, and,
   when abnormality is detected by the determiner, the controller controls the circulator to circulate the paper sheet and return the paper sheet to the reader.

3. The image inspection apparatus according to claim 1, wherein,
when a mismatch is detected as a result of comparison between the read image data and the output image data, and a mismatch is detected as a result of comparison between the circulated read image data and the output image data, and the respective mismatches have occurred at different pixels, the determiner determines that the image formed on the paper sheet is normal.

4. The image inspection apparatus according to claim 1, wherein,
when a mismatch is detected as a result of comparison between the read image data and the circulated read image data, or when a mismatch is detected as a result of comparison between a plurality of sets of the circulated read image data obtained through a plurality of circulating processes, the determiner eliminates the pixel from which the mismatch is detected from comparison objects.

5. The image inspection apparatus according to claim 1, further comprising
a shifter that shifts the paper sheet in a direction perpendicular to the paper sheet conveyance being performed by the conveyor, the direction being in a plane of the paper sheet,
wherein the shifter shifts the paper sheet by different amounts in a plurality of conveying processes being performed by the conveyor before and after circulation by the circulator.

6. The image inspection apparatus according to claim 5, wherein,
when a mismatch is detected as a result of comparison between the read image data and the output image data, and a mismatch is detected as a result of comparison between the circulated read image data and the output image data, and the respective mismatches have occurred at pixels in positions equivalent to the shifting performed by the shifter, the determiner senses abnormality of the reader, and determines that the image formed on the paper sheet is normal.

7. The image inspection apparatus according to claim 6, wherein,
when the respective mismatches have occurred at the same pixel, the determiner determines that the image formed on the paper sheet is abnormal.

8. The image inspection apparatus according to claim 1, further comprising
a reverser that reverses the paper sheet when conveyance is performed by the conveyor or when circulation is performed by the circulator,
wherein
the reader reads a first side and a second side of the paper sheet with different readers, and
the reader reads the image formed on the paper sheet with different readers during conveyance by the conveyor and during circulation by the circulator.

9. The image inspection apparatus according to claim 8, wherein,
when mismatches are detected as a result of comparison prior to circulation and comparison after the circulation, and the respective mismatches have occurred at different pixels, the determiner determines that the image formed on the paper sheet is normal, and,
when the respective mismatches have occurred at the same pixel, the determiner determines that the image formed on the paper sheet is abnormal.

10. The image inspection apparatus according to claim 1, wherein,
when the paper sheet is circulated by the circulator and is conveyed, the conveyor switches a conveyance speed to a lower speed, and,
when the paper sheet is circulated and conveyed, the reader generates the circulated read image data with a higher resolution than the read image data.

11. The image inspection apparatus according to claim 1, wherein,
after determining the reader to be abnormal, the determiner eliminates the pixel from which a mismatch has been detected due to the abnormality of the reader, and compares the pixels in the read image data with the corresponding pixels in the output image data, to determine whether the read image data matches the output image data.

12. An image forming system comprising:
an image forming apparatus that forms an image on a paper sheet, using output image data; and
the image inspection apparatus of claim 1.

* * * * *